US011583581B2

(12) United States Patent
Schroff et al.

(10) Patent No.: US 11,583,581 B2
(45) Date of Patent: Feb. 21, 2023

(54) METHODS OF TREATING A RETROVIRAL INFECTION (71) Applicant: GILEAD SCIENCES, INC., Foster City, CA (US)

(72) Inventors: Matthias Schroff, Berlin (DE); Manuel Schmidt, Berlin (DE); Kerstin Kapp, Berlin (DE); Alfredo Zurlo, Berlin (DE); Ole Schmeltz Sogaard, Berlin (DE); Martin Tolstrup, Berlin (DE); Rasmus Offersen, Berlin (DE)

(73) Assignee: Gilead Sciences, Inc., Foster City, CA (US)

( * ) Notice: Subject to any disclaimer, the term of this patent is extended or adjusted under 35 U.S.C. 154(b) by 582 days.

(21) Appl. No.: 15/760,424

(22) PCT Filed: Sep. 21, 2016

(86) PCT No.: PCT/EP2016/072385
§ 371 (c)(1),
(2) Date: Mar. 15, 2018

(87) PCT Pub. No.: WO2017/050806
PCT Pub. Date: Mar. 30, 2017

(65) Prior Publication Data
US 2020/0230234 A1    Jul. 23, 2020

(30) Foreign Application Priority Data
Sep. 21, 2015    (GB) ..................... 1516676

(51) Int. Cl.
A61K 39/39    (2006.01)
A61K 31/711   (2006.01)
C12N 15/113   (2010.01)
C12N 15/117   (2010.01)
A61K 39/00    (2006.01)

(52) U.S. Cl.
CPC ............ *A61K 39/39* (2013.01); *A61K 31/711* (2013.01); *C12N 15/117* (2013.01); *C12N 15/1132* (2013.01); *A61K 2039/55561* (2013.01); *C12N 2310/17* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 2,382,696 A | 8/1945 | De | |
| 2,699,718 A | 1/1955 | Wright | |
| 4,363,649 A | 12/1982 | Yamato et al. | |
| 5,663,153 A | 9/1997 | Hutcherson et al. | |
| 5,723,335 A | 3/1998 | Hutcherson et al. | |
| 5,750,669 A | 5/1998 | Roesch et al. | |
| 5,856,462 A | 1/1999 | Agrawal | |
| 6,251,666 B1 | 6/2001 | Beigelman | |
| 6,449,725 B2 | 9/2002 | Deenadhayalan et al. | |
| 6,589,940 B1 | 7/2003 | Raz et al. | |
| 6,737,066 B1 | 5/2004 | Moss | |
| 6,849,725 B2 | 2/2005 | Junghans et al. | |
| 6,849,726 B2 | 2/2005 | Usman et al. | |
| 6,977,245 B2 | 12/2005 | Klinman et al. | |
| 7,378,509 B2 | 5/2008 | Mcevoy et al. | |
| 7,501,503 B2 | 3/2009 | Damha et al. | |
| 7,517,862 B2 | 4/2009 | Agrawal et al. | |
| 7,635,468 B2 | 12/2009 | Brie et al. | |
| 7,674,777 B2 | 3/2010 | Krieg et al. | |
| 7,879,992 B2 | 2/2011 | Vickers et al. | |
| 8,017,591 B2 | 9/2011 | Brzezicha et al. | |
| 9,212,366 B2 | 12/2015 | Wittig et al. | |
| 9,345,754 B2 | 5/2016 | Brie et al. | |
| 9,422,564 B2 | 8/2016 | Dina et al. | |
| 9,499,815 B1 | 11/2016 | Schroff et al. | |
| 10,006,032 B2 | 6/2018 | Schroff et al. | |
| 10,487,333 B2 | 11/2019 | Schroff et al. | |
| 10,604,760 B2 | 3/2020 | Schroff et al. | |
| 2002/0095033 A1 | 7/2002 | Ramasamy et al. | |
| 2003/0050263 A1* | 3/2003 | Krieg ................ C07H 21/00 514/44 A |
| 2003/0125279 A1 | 7/2003 | Junghans et al. | |
| 2006/0183703 A1 | 8/2006 | Schroff et al. | |
| 2006/0241076 A1 | 10/2006 | Uhlmann et al. | |

(Continued)

FOREIGN PATENT DOCUMENTS

DE    10211558 A1    10/2003
EP     0855184 A1     7/1998

(Continued)

OTHER PUBLICATIONS

Carr et al., The Lancet, 2000, 356:1423-1430. (Year: 2000).*
Scheller et al., Journal of Biological Chemistry, 2004, 279(21):21897-21902. (Year: 2004).*
Communication issued by the Indian Patent Office in counterpart Indian Patent Application No. 6051/DELNP/2013, dated Nov. 9, 2017, 7 pages.
European Patent Office Search Report for EP1647518A1 and English translation thereof, dated Jan. 20, 2006, 2 pages.
International Preliminary Report on Patentability received for International Application No. PCT/EP2011/074033, dated Jul. 4, 2013, 7 pages.

(Continued)

*Primary Examiner* — Nicole Kinsey White
(74) *Attorney, Agent, or Firm* — Mintz, Levin, Cohn, Ferris, Glovsky and Popeo, P.C.

(57) ABSTRACT

The invention relates to a non-coding sequence of deoxyribonucleic acids comprising at least one sequence motif $N^1N^2CGN^3N^4$, wherein N is a nucleotide comprising A, C, T, or G, and C is deoxycytidine, G is deoxyguanosine, A is deoxyadenosine and T is deoxy-thymidine for the treatment of viral infections. In particular, the non-coding sequence of deoxyribonucleic acids is used in combination with antiretroviral therapy and/or histone de-acetylase inhibitors.

7 Claims, 5 Drawing Sheets
Specification includes a Sequence Listing.

(56) References Cited

U.S. PATENT DOCUMENTS

| | | |
|---|---|---|
| 2007/0049546 A1 | 3/2007 | Brzezicha et al. |
| 2007/0142315 A1 | 6/2007 | Forsbach et al. |
| 2007/0179101 A1 | 8/2007 | Kitagawa et al. |
| 2008/0131466 A1 | 6/2008 | Reed et al. |
| 2008/0260820 A1 | 10/2008 | Borrelly et al. |
| 2008/0311630 A1 | 12/2008 | Schroff et al. |
| 2009/0004703 A1 | 1/2009 | Schroff |
| 2009/0082295 A1 | 3/2009 | Jungnelius et al. |
| 2009/0136528 A1 | 5/2009 | Singh et al. |
| 2009/0169472 A1 | 7/2009 | Diebold et al. |
| 2009/0181078 A1 | 7/2009 | Reed et al. |
| 2010/0130593 A1 | 5/2010 | Garren et al. |
| 2010/0303803 A1 | 12/2010 | Schroff et al. |
| 2011/0098456 A1 | 4/2011 | Uhlmann et al. |
| 2014/0010830 A1 | 1/2014 | Schroff et al. |
| 2018/0251767 A1 | 9/2018 | Schroff et al. |
| 2019/0316134 A1 | 10/2019 | Schroff et al. |
| 2021/0010003 A1 | 1/2021 | Schroff et al. |
| 2021/0340543 A1 | 11/2021 | Schroff et al. |

FOREIGN PATENT DOCUMENTS

| | | |
|---|---|---|
| EP | 0941318 A1 | 9/1999 |
| EP | 1196178 B1 | 6/2004 |
| EP | 1776124 A1 | 4/2007 |
| EP | 2246433 A1 | 11/2010 |
| EP | 2333091 A2 | 6/2011 |
| EP | 2197488 B1 | 5/2014 |
| EP | 2655623 B1 | 2/2017 |
| EP | 2999787 B1 | 4/2017 |
| FR | 1418965 A | 11/1965 |
| FR | 2732971 A1 | 10/1996 |
| GB | 191115253 A | 6/1912 |
| GB | 684057 A | 12/1952 |
| GB | 2523187 A | 8/2015 |
| JP | 2002503212 A | 1/2002 |
| JP | 2003204793 A | 7/2003 |
| JP | 2012157312 A | 8/2012 |
| RU | 2351362 C2 | 4/2009 |
| WO | 9818810 A1 | 5/1998 |
| WO | 9821322 A1 | 5/1998 |
| WO | 0050075 A2 | 8/2000 |
| WO | 01/00232 A2 | 1/2001 |
| WO | 0107055 A1 | 2/2001 |
| WO | 0140515 A1 | 6/2001 |
| WO | 0226757 A2 | 4/2002 |
| WO | 02060476 A2 | 8/2002 |
| WO | 03004602 A2 | 1/2003 |
| WO | 03031469 A2 | 4/2003 |
| WO | 03031470 A2 | 4/2003 |
| WO | 03057822 A2 | 7/2003 |
| WO | 2004041183 A2 | 5/2004 |
| WO | 2005042018 A2 | 5/2005 |
| WO | 2005063280 A1 | 7/2005 |
| WO | 2005/080567 A1 | 9/2005 |
| WO | 2006002038 A2 | 1/2006 |
| WO | 2006015872 A1 | 2/2006 |
| WO | 2006091591 A1 | 8/2006 |
| WO | 2007047396 A2 | 4/2007 |
| WO | 2007089871 A2 | 8/2007 |
| WO | 2007131495 A2 | 11/2007 |
| WO | 2008153733 A2 | 12/2008 |
| WO | 2009035554 A2 | 3/2009 |
| WO | 2009/059805 A1 | 5/2009 |
| WO | 2009069447 A1 | 6/2009 |
| WO | 2009069682 A1 | 6/2009 |
| WO | 2010/039137 A1 | 4/2010 |
| WO | 2010125182 A1 | 11/2010 |
| WO | 2011/117408 A1 | 9/2011 |
| WO | 2012/085282 A1 | 6/2012 |
| WO | 2012085291 A1 | 6/2012 |
| WO | 2014191222 A1 | 12/2014 |
| WO | 2015124614 A1 | 8/2015 |
| WO | 2017042336 A1 | 3/2017 |
| WO | 2017050806 A1 | 3/2017 |
| WO | 2018193137 A1 | 10/2018 |
| WO | 2019043192 A1 | 3/2019 |
| WO | 2019043194 A1 | 3/2019 |

OTHER PUBLICATIONS

International Preliminary Report on Patentability received for International Application No. PCT/EP2016/071314, dated Mar. 22, 2018, 11 pages.

International Preliminary Report on Patentability received for International Application No. PCT/EP2016/072385, dated Apr. 5, 2018, 9 pages.

International Search Report and Written Opinion received for International Application No. PCT/EP2016/071314, dated Feb. 16, 2017, 17 pages.

International Search Report and Written Opinion received for International Application No. PCT/EP2011/074033, dated Mar. 27, 2012, 10 pages.

Luxembourg Search Report received for Luxembourg Application No. LU92S21, dated May 25, 2016, 12 pages.

Translation of the Notification of Reasons of Rejection dated Jan. 17, 2017, issued by the Japanese Patent Office in counterpart Japanese Application No. 2016-515715, 6 pages.

Wikibooks, "Structural Biochemistry/Organic Chemistry/Carbohydrates" Wikibooks entry, retrieved from https://en.wikibooks.org/w/index.php?title=Structural_Biochemistry/Organic_Chemistry/Carbohydrates&oldid=3176675 on Apr. 30, 2018, 6 pages.

Agrawal et al., "Antisense Therapeutics: is it as Simple as Complementary Base Recognition?", Molecular Medicine Today, Feb. 2000, vol. 6, pp. 72-81.

Blommers et al. (1994) "Effects of the Introduction of L-Nucleotides into DNA. Solution Structure of the Heterochiral Duplex d(G-C-G-(L)T-G-C-G).d(C-G-C-A-C-G-C) Studied by NMR Spectroscopy", Biochemistry, 1994, vol. 33, pp. 7886-7896.

Brassard et al., "Interferon-α as an Immunotherapeutic Protein", Journal of Leukocyte Biology, Apr. 2002, vol. 71, pp. 565-581.

Brown et al., "Effect of Phosphorothioate Modification of Oligodeoxynucleotides on Specific Protein Binding", Journal of Biological Chemistry, Oct. 28, 1994, vol. 269, No. 43, pp. 26801-26805.

Chen et al., "Generation and Analysis of Random Point Mutations in an Antibody CDR2 Sequence: Many Mutated Antibodies Lose their Ability to Bind Antigen", Journal of Experimental Medicine, Sep. 1992, vol. 176, pp. 855-866.

Clusel et al., "Ex Vivo Regulation of Specific Gene Expression by Nanomolar Concentration of Double-stranded Dumbbell Oligonucleotides", Nucleic Acids Research, 1993, vol. 21, No. 15, pp. 3405-3411.

Damha et al., "Antisense L/D-Oligodeoxynucleotide Chimeras: Nuclease Stability, Base-Pairing Properties, and Activity at Directing Ribonuclease H", Biochemistry, 1994, vol. 33, No. 25, pp. 7877-7885.

Doi et al., "Structural Characteristics of Enantiomorphic DNA: Crystal Analysis of Racemates of the d(CGCGCG) Duplex", Journal of the American Chemical Society, 1993, vol. 115, pp. 10432-10433.

Duraiswamy et al., "Therapeutic PD-1 Pathway Blockade Augments with Other Modalities of Immunotherapy T-Cell Function to Prevent Immune Decline in Ovarian Cancer", Cancer Research, Aug. 23, 2013, vol. 73, No. 23, pp. 6900-6912.

Erie et al., "A Dumbbell-shaped, Double-hairpin Structure of DNA: A Thermodynamic Investigation", Biochemistry, Nov. 1, 1987, vol. 26, No. 22, pp. 7150-7159.

Fourcade et al., "PD-1 and TIM-3 Regulate the Expansion of Tumor Antigen-Specific COB+ T Cells Induced by Melanoma Vaccines", Cancer Research, Dec. 16, 2013, vol. 74, No. 4, pp. 1045-1055.

Fraser et al., "The Serum Mannose-binding Protein and the Macrophage Mannose Receptor are Pattern Recognition Molecules that Link Innate and Adaptive Immunity", Seminars in Immunology, Oct. 1998, vol. 10, pp. 363-372.

(56) References Cited

OTHER PUBLICATIONS

Garbesi et al., "L-DNAs as Potential Antimessenger Oligonucleotides: A Reassessment", Nucleic Acids Research, 1993, vol. 21, No. 18, pp. 4159-4165.
Gonzalo et al., "A Heterologous Prime-boost Regime using DNA and Recombinant Vaccinia Virus Expressing the Leishmania Infantum P36/LACK Antigen Protects BALB/c Mice from Cutaneous Leishmaniasis", Vaccine, 2002, vol. 20, Nos. 7-8, pp. 1226-1231.
Goodchild, John, "Conjugates of Oligonucleotides and Modified Oligonucleotides: A Review of their Synthesis and Properties", Bioconjugate Chemistry, May/Jun. 1990, vol. 1, No. 3, pp. 165-187.
Harcourt et al., "Modulation of Double-stranded RNA-mediated Gene Induction by Interferon in Human Umbilical Vein Endothelial Cells", Journal of Interferon and Cytokine Research, 2000, vol. 20, pp. 1007-1013.
Hayashi et al., "Application of L-DNA as a Molecular Tag", Nucleic Acids Symposium Series, 2005, vol. 49, pp. 261-262.
Hayashi et al., "Detection of L-DNA-tagged PCR Products by Surface Plasmon Resonance Imaging", ChemBioChem, Jan. 22, 2007, vol. 8, pp. 169-171.
Hayashi et al., "Genotyping by Allele-specific L-DNA-tagged PCR", Journal of Biotechnology, 2008, vol. 135, pp. 157-160.
Heikenwalder et al., "Lymphoid Follicle Destruction and immunosuppression after Repeated CpG Oligodeoxynucleotide Administration", Nature Medicine, Feb. 2004, vol. 10, No. 2, pp. 187-192.
Hosono et al., "Properties of Base-pairing in the Stem Region of Hairpin Antisense Oligonucleotides Containing 2'-methoxynucleosides", Biochimica et Biophysica Acta—General Subjects, Jun. 9, 1995, vol. 1244, pp. 339-344.
Kapp et al., "Genuine Immunomodulation With dSLIM", Molecular Therapy-Nucleic Acids, Jun. 2014, vol. 3, No. 6, pp. e170.
Kim et al., "Superior Structure Stability and Selectivity of Hairpin Nucleic Acid Probes with an L-DNA Stem", Nucleic Acids Research, Oct. 24, 2017, vol. 35, No. 21, pp. 7279-7287.
Köchling et al., "Protection of Mice against Philadelphia Chromosome-positive Acute Lymphoblastic Leukemia by Cell-based Vaccination Using Nonviral, Minimalistic Expression Vectors and Immunomodulatory Oligonucleotides", Clinical Cancer Research, Aug. 1, 2003, vol. 9, pp. 3142-3149.
Koechling et al., "Optimization of DNA vaccine strategies protects mice against syngeneic Ph+ ALL", Blood, Nov. 16, 2003, vol. 102, No. 11, p. 746a, Abstract.
Kovarik et al., "CpG Oligodeoxynucleotides Can Circumvent the Th2 Polarization of Neonatal Responses to Vaccines But May Fail to Fully Redirect Th2 Responses Established by Neonatal Priming1", The Journal of Immunology, 1999, vol. 162, pp. 1611-1617.
Krieg et al., "Causing a Commotion in the Blood: Immunotherapy Progresses From Bacteria to Bacterial DNA", Immunol Today, Oct. 2000, vol. 21, No. 10, pp. 521-526.
Krieg et al., "CpG motifs in bacterial DNA trigger direct B-cell activation", Nature, Apr. 6, 1995, vol. 374, No. 6522, pp. 546-549.
Krieg et al., "Oligodeoxynucleotide Modifications Determine the Magnitude of B Cell Stimulation by CpG Motifs", Antisense and Nucleic Acid Drug Development, 1996, vol. 6, No. 2, pp. 133-139.
Krieg et al., "P-Chirality-Dependent Immune Activation by Phosphorothioate CpG Oligodeoxynucleotides", Oligonucleotides, 2003, vol. 13, No. 6, pp. 491-499.
Krieg et al., "Sequence Motifs in Adenoviral DNA Block Immune Activation by Stimulatory CpG Motifs", Proceedings of the National Academy of Sciences, Oct. 1998, vol. 95, pp. 12631-12636.
Krieg, Arthur M., "CpG DNA: A Pathogenic Factor in Systemic Lupus Erythematosus?", Journal of Clinical Immunology, 1995, vol. 15, No. 6, pp. 284-292.
Krieg, Arthur M., "CpG Motifs: The Active Ingredient in Bacterial Extracts?", Nature Medicine, Jul. 2003, vol. 9, No. 7, pp. 831-835.
Krieg, Arthur M., "Development of TLR9 Agonists for Cancer Therapy", The Journal of Clinical Investigation, May 2007, vol. 117, No. pp. 1184-1194.

Krieg, Arthur M., "Therapeutic Potential of Toll-like Receptor 9 Activation", Nature Reviews | Drug Discovery, Jun. 2006, vol. 5, No. 6, pp. 471-484.
Krishnamachari et al., "Innovative Strategies for Co-delivering Antigens and CpG oligonucleotides", Advanced Drug Delivery Reviews, 2009, vol. 61, No. 3, pp. 205-217.
Kulkarni et al., "Costimulatory Activation of Murine Invariant Natural Killer T Cells by Toll-like Receptor Agonists", Cellular Immunology, 2012, vol. 27, pp. 33-43.
Lai et al., "Comparison of D-G3139 and its Enantiomer L-G3139 in Melanoma Cells Demonstrates Minimal In Vitro but Dramatic In Vivo Chiral Dependency", The American Society of Gene Therapy, Feb. 2007, vol. 15, No. 2, pp. 270-278.
Lee et al., "IL-8 Reduced Tumorigenicity of Human Ovarian Cancer In Vivo Due to Neutrophil Infiltration", The Journal of Immunology, 2000, vol. 164, pp. 2769-2775.
Leva et al., "GnRH Binding RNA and DNA Spiegelmers: A Novel Approach Toward GnRH Antagonism", Chemistry & Biology, Mar. 2002, vol. 9, No. 3, pp. 351-359.
Levin, Arthur A., "A Review of the Issues in the Pharmacokinetics and Toxicology of Phosphorothiate Antisense Oligonucleotides", Biochimica et Biophysica Acta (BBA)—Gene Structure and Expression, 1999, vol. 1489, No. 1, pp. 69-84.
Lim et al., "Sequence-Independent Inhibition of RNA Transcription by DNA Dumbbells and Other Decoys", Nucleic Acids Research, 1997, vol. 25, pp. 575-581.
Lin et al., "Mirror Image DNA Nanostructures for Chiral Supramolecular Assemblies", Nano Letters, Jan. 2009, vol. 9, No. 1, pp. 433-436(8 pages).
Liu et al., "Immunostimulatory CpG Oligodeoxynucleotides Enhance the Immune Response to Vaccine Strategies Involving Granulocyte-macrophage Colony-stimulating Factor", Blood, Nov. 15, 1998, vol. 92, No. 10, pp. 3730-3736.
Mangsbo, Sara, "Immunological Checkpoint Blockade and TLR Stimulation for Improved Cancer Therapy", Acta Universitatis Upsaliensis Uppsala, Dec. 15, 2009, 1-84.
Marabelle et al., "Depleting Tumor-specific Tregs at a Single Site Eradicates Disseminated Tumors", Journal of Clinical Investigation, Jun. 2013, vol. 123, No. 6, pp. 2447-2463.
Marshall et al., "Novel Chimeric Immunomodulatory Compounds Containing Short CpG Oligodeoxyribonucleotides have Differential Activities in Human Cells", Nucleic Acids Research, 2003, vol. 31, No. 1, pp. 5122-5133.
Mathews et al., "Excerpt from "Biochemistry" Chapter 4: Nucleic Acid", The Benjamin Cummings Publishing Company, Inc., 1990, pp. 108-111.
McCluskie et al., "Route and Method of Delivery of DNA Vaccine Influence Immune Responses in Mice and Non-Human Primates", Molecular Medicine, 1999, vol. 5, pp. 287-300.
McNaught et al. (1997), Definition of Configuration (stereochemical), IUPAC Compendium of Chemical Terminology, 2nd ed. (the "Gold Book"), Blackwell Scientific Publications; Oxford, 1 page.
Medzhitov, Ruslan, "Toll-like Receptors and Innate Immunity", Nature Reviews | Immunology, Nov. 2001, vol. 1, No. 2, pp. 135-145.
Melief et al., "T-cell Immunotherapy of Cancer", Research in Immunology, Jun.-Aug. 1991, vol. 142, Nos. 5-6, pp. 425-429.
Miller et al., "Transduction of Human Melanoma Cell Lines with the Human Interleukin-7 Gene Using Retroviral-mediated Gene Transfer: Comparison of Immunologic Properties with Interleukin-2", Blood, Dec. 1993, vol. 82, Vo. 12, pp. 3686-3694.
Moelling, K., "Naked DNA—the Poor Man's Gene Therapy?", Gene Therapy, 1998, vol. 5, pp. 573-574.
Moreno et al., "Toll-like Receptor Agonists and Invariant Natural Killer T-cells Enhance Antibody-dependent Cell-mediated Cytotoxicity (ADCC", Cancer Letters, 2008, vol. 272, No. 1, pp. 70-76.
Moseman et al., "Human Plasmacytoid Dendritic Cells Activated by CpG Oligodeoxynucleotides Induce the Generation of CD4+CD25+ Regulatory T Cells", The Journal of Immunology, 2004, vol. 173, pp. 4433-4442.
Noguchi et al., "Induction of Antitumor Immunity by Transduction of CD40 Ligand Gene and Interferon-γ Gene into Lung Cancer", Cancer Gene Therapy, 2001, vol. 8, No. 6, pp. 421-429.

(56) References Cited

OTHER PUBLICATIONS

Ohno et al., "Antigen-binding Specificities of Antibodies are Primarily Determined by Seven Residues of VH", Proceedings of the National Academy of Sciences, May 1985, vol. 82, pp. 2945-2949.
Paillard, Florence, "The Search for the "Best" Cytokine to Induce Antitumor Immunity", Human Gene Therapy, Nov. 20, 1998, vol. 9, pp. 2457-2458.
Pasternak et al., "Chronic Myelogenous Leukemia: Molecular and Cellular Aspects", Journal of Cancer Research and Clinical Oncology, 1998, vol. 124, pp. 643-660.
Pelicano et al., "Excision of Beta-D- and Beta-L-nucleotide Analogs from DNA by the Human Cytosolic 3'-to-5' Exonuclease", Molecular Pharmacology, May 2000, vol. 57, pp. 1051-1055.
Purschke et al., "A DNA Spiegelmer to *Staphylococcal* Enterotoxin B", Nucleic Acids Research, Jun. 15, 2003, vol. 31, No. 12, pp. 3027-3032.
Riera-Knorrenschild et al., "Maintenance with the TLR-9 Agonist MGN1703 versus Placebo in Patients with Advanced Colorectal Carcincoma (mCRC): A Randomized Phase II Trial (IMPACT).", Journal of Clinical Oncology, May 2013, 31(15_suppl):3643.
Rudikoff et al., "Single Amino Acid Substitution Altering Antigen-Binding Specificity", Proceedings of the National Academy of Sciences, Mar. 1, 1982, vol. 79, pp. 1979-1983.
Rutz et al., "Toll-like Receptor 9 Binds Single-stranded CpG-DNA in a Sequence- and pH-dependent Manner", European Journal of Immunology, 2004, vol. 34, pp. 2541-2550.
Schakowski et al., "A Novel Minimal-Size Vector (MIDGE) Improves Transgene Expression in Colon Carcinoma Cells and Avoids Transfection of Undesired DNA", Molecular Therapy, May 2001, vol. 3, No. 5, pp. 793-800.
Schirmbeck et al., "Priming of Immune Responses to Hepatitis B Surface Antigen with Minimal DNA Expression Constructs Modified with a Nuclear Localization Signal Peptide", Journal of Molecular Medicine, 2001, vol. 79, pp. 343-350.
Schmidt et al., "Combination of TLR9 Agonist Lefitolimod/ MGN1703 with Checkpoint Inhibitors for Cancer Immunotherapy", Journal of Clinical Oncology, Feb. 1, 2017, vol. 35, No. 4, pp. 634-634.
Schmidt et al., "Cytokine and Ig-production by CG-containing Sequences with Phosphorodiester Backbone and Dumbbell-shape", Allergy, 2006, vol. 61, pp. 56-63.
Schmidt et al., "Immune-Modulatory Function of CPG Sequence Motifs in Covalently-Closed, Double-Stem-Loop DNA Constructs (dSLIM)", Blood, Nov. 16, 2003, vol. 102, No. 11, pp. 769a-770a.
Schmidt et al., "TLR9 agonist lefitolimod to improve antitumor effect of checkpoint inhibitors in vivo", Journal of Clinical Oncology, 2017, vol. 35, No. 15, 1 page.
Schmoll et al, "Updated results of the randomized phase 2 impact trial: maintenance with TLR-9 agonist MGN1703 vs placebo in patients with metastatic colorectal carcinoma (MCRC)", Annals of Oncology, 2013, vol. 24, No. 4, iv11-iv24.
Seder et al., "Acquisition of lymphokine-producing phenotype by CD4+ T cells", Annual Review of Immunology, 1994, vol. 12, pp. 635-673.
Shaffer, Anita T., "Immunotherapy Doubts Fading in GI Cancers", Conference | School of Gastrointestinal Oncology, Apr. 26, 2016, https://www.onclive.com/view/immunotherapy-doubts-fading-in-gi-cancers, 4 pages.
Sheehan et al., "Phosphorothioate Oligonucleotides Inhibit the Intrinsic Tenase Complex", Blood, Sep. 1, 1998, vol. 92, No. 5, pp. 1617-1625.
Sin et al., "Interleukin 7 Can Enhance Antigen-Specific Cytotoxic-T-Lymphocyte and/or Th2-Type Immune Responses In Vivo", Clinical and Diagnostic Laboratory Immunology, Sep. 2000, vol. 7, No. 5, pp. 751-758.
Singh et al., "Recent Developments in Oligonucleotide Conjugation", Chemical Society Reviews, 2010, vol. 39, pp. 2054-2070.
Sun et al., "In Vivo Gene Transferor CD40 Ligand into Colon Cancer Cells Induces Local Production of Cytokines and Chemokines, Tumor Eradication and Protective Antitumor Immunity", Gene Therapy, 2000, vol. 7, pp. 1467-1476.
Surman et al., "Generation of Polyclonal Rabbit Antisera to Mouse Melanoma Associated Antigens Using Gene Gun Immunization", Journal of Immunological Methods, May 1, 1998, vol. 214, Nos. 1-2, pp. 51-62.
Susonov et al., "Stereochemical Control of DNA Biosynthesis", Nucleic Acids Research, 2000, vol. 28, No. 5, pp. 1170-1175.
Tarhini et al., "Differing Patterns of Circulating Regulatory T-Cells and Myeloid Derived Suppressor Cells in Metastatic Melanoma Patients Receiving Anti-CTLA4 Antibody and Interferon-α or TLR-9 Agonist and GM-CSF with Peptide Vaccination", Journal of Immunotherapy, Nov. 2012, vol. 35, No. 9, pp. 702-710.
Tondelli et al., "Terminally L-modified Oligonucleotides: Pairing, Stability and Biological Properties", Anti-Cancer Drugs, 1996, vol. 7, pp. 189-194.
Urata et al., "NMR Study of a Heterochiral DNA: Stable Watson-Crick-Type base-pairing between the Enantiomeric Residues", Journal of the American Chemical Society, 1993, vol. 115, pp. 9852-9853.
Vater et al., "Turning Mirror-image Oligonucleotides into Drugs: The Evolution of Spiegelmer(®) Therapeutics", Drug Discovery Today, Jan. 2015, vol. 20, No. 1, pp. 147-155.
Vereecque et al., "Gene Transfer of GM-CSF, CD80 and CD154 cDNA Enhances Survival in a Murine Model of Acute Leukemia with Persistence of a Minimal Residual Disease", Gene Therapy, 2000, vol. 7, No. 15, pp. 1312-1316.
Verthelyi et al., "Human Peripheral Blood Cells Differentially Recognize and Respond to Two Distinct CpG Motifs", The Journal of Immunology, 2001, vol. 166, pp. 2372-2377.
Vibholm et al., "Short-Course Toll-Like Receptor 9 Agonist Treatment Impacts Innate Immunity and Plasma Viremia in Individuals with Human Immunodeficiency Virus Infection", Clinical Infectious Diseases, Jun. 15, 2017, vol. 64, pp. 1686-1695.
Walker et al., "Immunostimulatory oligodeoxynucleotides promote protective immunity and provide systemic therapy for leishmaniasis via IL-12- and IFN-γ-dependent mechanisms", Proceedings of the National Academy of Sciences, Jun. 1999, vol. 96, pp. 6970-6975.
Wang et al., "CpG-Independent Synergistic Induction of βChemokines and a Dendritic Cell Phenotype by Orthophosphorothioate Oligodeoxynucleotides and Granulocyte-Macrophage Colony-Stimulating Factor in Elutriated Human Primary Monocytes", The Journal of Immunology, Jun. 2005, vol. 174, No. 10, pp. 6113-6121.
Weber et al., "Tumor Immunity and Autoimmunity Induced by Immunization with Homologous DNA", Journal of Clinical Investigation, Sep. 1998, vol. 102, No. 6, pp. 1258-1264.
Weeratna et al., "Reduction of Antigen Expression from DNA Vaccines by Coadministered Oligodeoxynucleotides", Antisense and Nucleic Acid Drug Development, 1998, vol. 8, No. 4, pp. 351-356.
Weihrauch et al., "Phase I Clinical Study of the Toll-like Receptor 9 Agonist MGN1703 in Patients with Metastatic Solid Tumours", European Journal of Cancer, 2015, vol. 51:146-156.
Weiner et al., "The Immunobiology and Clinical Potential of Immunostimulatory CpG Oligodeoxynucleotides", Journal of Leukocyte Biology, Oct. 2000, vol. 68, pp. 455-463.
Williams et al., "Bioactive and Nuclease-resistant L-DNA Ligand of Vasopressin", Proceedings of the National Academy of Sciences, Oct. 1997, vol. 94, pp. 11285-11290.
Wittig et al., "Therapeutic Vaccination Against Metastatic Carcinoma by Expression-modulated and Immunomodified Autologous Tumor Cells: A First Clinical Phase I/II Trial", Human Gene Therapy, Feb. 10, 2001, vol. 12, pp. 267-278.
Wlotzka et al., "In Vivo Properties of an Anti-GnRH Spiegelmer: An Example of an Oligonucleotide-based Therapeutic Substance Class", Proceedings of the National Academy of Sciences, Jun. 25, 2002, vol. 99, No. 13, pp. 8898-8902.
Wolchok et al., "Guidelines for the Evaluation of Immune Therapy Activity in Solid Tumors: Immune-Related Response Criteria", Clinical Cancer Research, 2009, vol. 15, No. 23, pp. 7412-7420(10 pages).

(56) References Cited

OTHER PUBLICATIONS

Wolters et al., "Construction of a 42 Base Pair Double Stranded DNA Microcircle", Nucleic Acids Research, Jul. 11, 1989, vol. 17, No. 13, pp. 5163-5172.
Wong et al., "TLR-9 Signaling and TCR Stimulation Co-Regulate CD8+ T Cell-Associated PD-1 Expression", Immunology Letters, 2009, vol. 127, No. 1, pp. 60-67.
Wu et al., "Natural Killer T Cells and Autoimmune Disease", Current Molecular Medicine, 2009, vol. 9, pp. 4-14.
Zachariae et al, "Properties of Monocyte Chemotactic and Activating Factor (MCAF) Purified From a Human Fibrosarcoma Cell Line", The Journal of Experimental Medicine, Jun. 1990, vol. 171, pp. 2177-2182.
Zdrazilova-Dubska et al., "NKT-like Cells are Expanded in Solid Tumour Patients", Klinicka Onkologie, 2012, 25(Suppl. 2):2S21-2S25.
Zhao et al., "Comparison of Cellular Binding and Uptake of Antisense Phosphodiester, Phosphorothioate, and Mixed Phosphorothioate and Methylphosphonate Oligonucleotides", Antisense Research and Development, 1993, vol. 3, pp. 53-66.
Zhao et al., "Site of Chemical Modifications in CpG Containing Phosphorothioate Oligodeoxynucleotide Modulates its Immunostimulatory Activity", Bioorganic & Medicinal Chemistry Letters, 1999, vol. 9, pp. 3453-3458.
Priya Aggarwal et al., "Augmentation of HIV-1 Subtype C Vaccine Constructs Induced Immune Response in Mice by CpG Motif 1826-ODN", Viral Immunology, Mar. 2005, pp. 213-223, vol. 18, No. 1.
Peter Silvera et al., "Vaccination with gp 120-depleted HIV-1 plus immunostimulatory CpG oligodeoxynucleotides in incomplete Freund's adjuvant stimulates cellular and humoral immunity in rhesus macaques", Dec. 21, 2004, pp. 827-839, vol. 23, No. 6.
Mila Ayash-Rashkovsky et al., "Generation of Th1 immune responses to inactivated, gp 120-depleted HIV-1 in mice with a dominant Th2 biased immune profile via immunostimulatory oligonucleotides—relevance to AIDS vaccines in developing countries", Jun. 1, 2002, pp. 2684-2692, vol. 20, No. 21-22.
GB1516676.2 United Kingdom Search Report, dated Jul. 7, 2016, pp. 18-19.
"Toll-like Receptor 9 Agonist Treatment in Chronic HIV-1 Infection (TEACH)", ClinicalTrials.gov, website, May 13, 2015, 3 pages, Trial No. NCT02443935.
"Toll-like receptor 9 enhancement of antiviral immunity in chronic HIV-1 infection: a phase 1b/2a trial (TEACH)", EU Clinical Trails Register, Apr. 7, 2015, 4 pages, EudraCT No. 2014-005634-59.
R. Offersen, et al., "A novel TLR-9 agonist (MGN1703) activates NK-cells and enhances NK-cell mediated viral killing of HIV-1 infected CD4+ T cells ex vivo", Towards an HIV Cure Symposium, Jul. 18-19, 2015, 113 pages.
Burghardt Wittig et al., "MGN1703, an immunomodulator and toll-like receptor 9 (TLR-9) agonist: From bench to bedside", Critical Reviews in Oncology/Hematology, 2015, pp. 31-44, vol. 94.
Manuel Schmidt, et al., "Design and Structural Requirements of the Potent and Safe TLR-9 Agonistic Immunomodulator MGN1703", Nucleic Acid Therapeutics, Mar. 31, 2015, pp. 130-140, vol. 25, No. 3.
Guey-Chuen Perng, et al., "Towards an Understanding of the Herpes Simplex Virus Type 1 Latency-Reactivation Cycle", Interdisciplinary Perspectives on Infectious Diseases, pp. 1-19, vol. 2010.
Justin Bailey et al., "Mechanisms of HIV-1 escape from immune responses and antiretroviral drugs", Current Opinion in Immunology, 2004, pp. 470-476, vol. 16.
NM Archin et al., "Administration of vorinostat disrupts HIV-1 latency in patients on antiretroviral therapy", Nature, Jul. 8, 2013, pp. 482-485, vol. 487(7408).
Thomas Aagaard Rasmussen et al., "Comparison of HDAC inhibitors in clinical development", Human Vaccines & Immunotherapeutics, May 2013, pp. 993-1001, vol. 9, Issue 5.
Liang Shan et al., "Stimulation of HIV-1-Specific CytolyticT Lymphocytes Facilitates Elimination of Latent Viral Reservoir after Virus Reactivation", Immunity Article, Mar. 23, 2012, pp. 491-501, vol. 36, No. 3.
Nicole C. Hauser et al., "Utilising the left-helical conformation of L-DNA for analysing different marker types on a single universal microarray platform", Nucleic Acids Research, Sep. 20, 2006, pp. 5101-5111, vol. 34.
Hidehito Urata et al., "Synthesis and properties of mirror-image DNA", Nucleic Acids Research, 1992, pp. 3325-3332, vol. 20, No. 13.
International Search Report for PCT/EP2016/072385 dated Dec. 16, 2016 [PCT/ISA210].
Written Opinion for PCT/EP2016/072385 dated Dec. 16, 2016 [PCT/ISA/237].
International Search Report and Written Opinion for International Patent Application No. PCT/DE04/01096, dated Nov. 12, 2004, 17 pages.
International Preliminary Examination Report for PCT International Application No. PCT/DE04/01096, dated Oct. 4, 2006, 10 pages.
International Search Report received for International Patent Application No. PCT/DE2000/00565, dated Aug. 18, 2000, 6 pages (English Translation Attached).
International Preliminary Examination Report for PCT International Application No. PCT/DE00/00565, completed on Oct. 23, 2001, 9 pages (English Translation Attached).
Agrawal et al. (Mar. 1, 2002) "Medicinal Chemistry and Therapeutic Potential of CpG DNA", Trends in Molecular Medicine, 8(3):114-121.
Guiducci et al. (2009) "Signalling Pathways Leading to IFN-alpha Production in Human Plasmacytoid Dendritic Cell and the Possible Use of Agonists or Antagonists of TLR7 and TLR9 in Clinical Indications", Journal of Internal Medicine, 265(1):43-57.
Hartmann et al. (Mar. 2000) "Delineation of a CpG Phosphorothioate Oligodeoxynucleotide for Activating Primate Immune Responses In Vitro and In Vivo", The Journal of Immunology, 164(3):1617-1624.
Klinman Dennis M. (2004) "Immunotherapeutic Uses of CpG Oligodeoxynucleotides", Nature Reviews Immunology, 4(4):249-259(10 pages).
Klinman et al. (Jun. 2004) "Use of CpG Oligodeoxynucleotides as Immune Adjuvants", Immunological Reviews, 199(1):201-216.
Krieg Arthur M. (Apr. 2004) "Antitumor Applications of Stimulating Toll-like Receptor 9 with CpG Oligodeoxynucleotides", Current Oncology Reports, 6(2):88-95.
Krieg Arthur M. (Nov. 1998) "The CpG Motif: Implications for Clinical Immunology", BioDrugs, 10(5):341-346.
Watanabe et al. (Jun. 2008) "Endogenous siRNAs from Naturally Formed dsRNAs Regulate Transcripts in Mouse Oocytes", Nature, 453(7194):539-544.
Yamamoto et al. (Jan. 1994) "Ability of Oligonucleotides with Certain Palindromes to Induce Interferon Production and Augment Natural Killer Cell Activity is Associated with Their Base Length", Antisense Research and Development, 4(2):119-122.
Zhao et al. (Jan. 1996) "Effect of Different Chemically Modified Oligodeoxynucleotides on Immune Stimulation", Biochemical Pharmacology, 51(2):173-182.
Osterlehner et al. (Nov. 2011) "Promoter Methylation and Transgene Copy Numbers Predict Unstable Protein Production in Recombinant Chinese Hamster Ovary Cell Lines", Biotechnology and Bioengineering, 108(11):2670-2681.
Muller S. (2008) "Nucleic Acids from A to Z: A Concise Encyclopedia", Wiley-VCH: D Weinheim, Germany, pp. 68, 71, 86, 5 pages.
Roitt et al. (1998) "Chapter 19: Vaccination", In Immunology (5th ed.). Mosby: London, 13 pages.
Roitt et al. (1998) "Chapter 20: Tumour Immunology", In Immunology (5th ed.). Mosby: London, 11 pages.

* cited by examiner

SEQUENCE LISTING

<160> NUMBER OF SEQ ID NOS: 5

<210> SEQ ID NO 1
<211> LENGTH: 48
<212> TYPE: DNA
<213> ORGANISM: Artificial Sequence
<220> FEATURE:
<223> OTHER INFORMATION: Synthetic nucleotide sequence

<400> SEQUENCE: 1
gttcctggag acgttcttag gaacgttctc cttgacgttg gagagaac                    48

<210> SEQ ID NO 2
<211> LENGTH: 60
<212> TYPE: DNA
<213> ORGANISM: Artificial Sequence
<220> FEATURE:
<223> OTHER INFORMATION: Synthetic nucleotide sequence

<400> SEQUENCE: 2
accttccttg tactaacgtt gcctcaagga aggttgatct tcataacgtt gcctagatca      60

<210> SEQ ID NO 3
<211> LENGTH: 18
<212> TYPE: DNA
<213> ORGANISM: Artificial Sequence
<220> FEATURE:
<223> OTHER INFORMATION: Synthetic nucleotide sequence

<400> SEQUENCE: 3
aacgttcttc ggggcgtt                                                    18

<210> SEQ ID NO 4
<211> LENGTH: 58
<212> TYPE: DNA
<213> ORGANISM: Artificial Sequence
<220> FEATURE:
<223> OTHER INFORMATION: Synthetic nucleotide sequence

<400> SEQUENCE: 4
aggtggtaac ccctaggggt taccaccttc atcgtcgttt tgtcgttttg tcgttctt        58

<210> SEQ ID NO 5
<211> LENGTH: 116
<212> TYPE: DNA
<213> ORGANISM: Artificial Sequence
<220> FEATURE:
<223> OTHER INFORMATION: Synthetic nucleotide sequence

<400> SEQUENCE: 5
cctaggggtt accaccttca ttggaaaacg ttcttcgggg cgttcttagg tggtaacccc      60
taggggttac caccttcatt ggaaaacgtt cttcggggcg ttcttaggtg gtaacc         116

METHODS OF TREATING A RETROVIRAL INFECTION

CROSS REFERENCE TO RELATED APPLICATIONS

This application is a National Stage of International Application No. PCT/EP2016/072385, filed Sep. 21, 2016, claiming priority based on Great British Patent Application No. 1516676.2, filed Sep. 21, 2015.

FIELD OF THE INVENTION

The invention relates to a combination and its use for the treatment of diseases like viral infections.

BRIEF DESCRIPTION OF THE RELATED ART

The term "immunotherapy" defines the treatment of diseases by stimulating, inducing, enhancing or suppressing an immune response. The strategy of immuno-therapies is to fight diseases, such as cancer, infectious diseases, allergy and asthma by activating the immune system.

Viral infection may result in a state called viral latency, which is characterized by a state of reversible non-productive infection of individual cells. Viral latency provides an important mechanism for viral persistence and escape from immune recognition (Perng and Jones, Interdiscip Perspect Infect Dis, 2010, p 262415).

It is known that Herpes viruses for instance use genetic programs that allow persistence of their viral genomes with minimal viral gene expression. For retroviruses, stable integration of reverse transcribed viral cDNA into the host cell genome is an important step towards the persistence of viral genomes for the lifespan of the infected cells. There are retroviruses which establish a state of latent infection. The term latency was initially used for HIV-1 in the clinical sense to describe the long asymptomatic period between initial infection and development of AIDS. However, it became clear that HIV-1 replicates actively throughout the progress of infection, even during the asymptomatic period. One of the major mechanism by which HIV-1 escapes from immune response is through rapid evolution of escape mutations that abrogate recognition by neutralizing antibodies and cytolytic T lymphocytes (Bailey et al., Curr Opin Immunol 16, p. 470-476, 2004). Nevertheless, it has become clear that HIV-1 can establish a state of latent infection at the level of individual T cells. Thus, the removal of the latency reservoir could be a major factor in improving the therapy of HIV.

Antiretroviral therapy (ART) refers to medications for the treatment of retroviral infections like HIV infections. The drugs do not abolish the virus so that patients will be virus-free after treatment. However, when the drugs—or a selection of them is given in combination they may prevent the growth of the virus. When the virus is slowed down, so is HIV disease. Antiretroviral drugs are referred to as ARV. Combination ARV therapy (cART) is referred to as highly active ART(HAART).

ARV drugs attack HIV in different ways and they are divided in so-called classes. The first class of anti-HIV drugs which were developed are the "nucleoside reverse transcriptase inhibitors" (also called NRTIs or "nukes".) These drugs block the use of HIV's genetic material to create DNA from RNA. AZT is the most prominent member of this class.

Another class are the "non-nucleoside reverse transcriptase inhibitors", also called non-nukes or NNRTIs, which also block the transcription of RNA into DNA.

Members belonging to the class of "protease inhibitors" block the step of cutting raw material for new HIV virus into specific pieces. Finally, there is the class of "entry inhibitors" preventing HIV from entering a cell, and the class of "HIV integrating inhibitors", preventing the integration of HIV genetic material into the host genome. Within the meaning of the present disclosure cART refers to the combinatorial use of at least two member of these classes of ARV.

Recently it was shown that the state of HIV-1 latency can be disrupted safely in patients with combination antiretroviral therapy (cART) by latency reversing agents (LRA), particularly histone de-acetylase inhibitors (HDACi) (Archin et al., 2012, Nature 487(7408):482-485; Rasmussen et al., 2013, Hum Vaccin Immunother 9(5)). However, it became obvious in the majority of patients that reactivation of latently infected cells alone does not reduce the HIV-1 reservoir. This seems to be related to insufficient immune mediated killing of reactivated cells. However, the activation of the innate and adaptive immunity bears the risk of activating HIV-infected cells so that the disease will progress. Thus, it is questionable whether the activation of the immune system will help HIV patients.

The concept of immunotherapy-supported HIV treatment is supported by a recent in vitro study showing that CD8+ T cells from cART-treated aviremic HIV patients are capable of killing reactivated infected autologous CD4+ T cells but only when the CD8+ T cells have been antigen-stimulated prior to co-culture (Shan et al., 2012, Immunity 36(3):491-501).

Thus, there is a need for compounds which will expose the latent reservoir of HIV infected cells through their activation and targeting of the reactivated cells for immune mediating killing through pharmacological interventions.

Based on this state of the art, the objective of the instant disclosure is to provide immunostimulating compounds for reactivating latent HIV infected cells and their recognition and destruction by the immune system, and their use as a medicament.

SUMMARY OF THE INVENTION

With regard to the prior art it is an objective of the instant disclosure to provide a non-coding sequence of deoxyribonucleic acids comprising at least one sequence motif $N^1N^2CGN^3N^4$, wherein N is a nucleotide comprising A, C, T, or G, and C is deoxycytidine, G is deoxyguanosine, A is deoxyadenosine and T is deoxythymidine for the treatment of viral infections.

It is intended to use the non-coding sequence of deoxyribonucleic acids of the present invention in combination with combination antiretroviral therapy and/or histone de-acetylase inhibitors in viral infections, wherein the viral infection may be latent.

The non-coding sequence of deoxyribonucleic acids of the instant disclosure is intended to be provided for the treatment of HIV-1, in particular for the treatment of latent HIV-1 infection.

With the non-coding sequence of deoxyribonucleic acids of the present disclosure, $N^1N^2$ may be an element taken from the group of GT, GG, GA, AT and AA, $N^3N^4$ may be an element taken from the group of CT, TG and TT.

The non-coding sequence of deoxyribonucleic acids can be either linear open-chained on both sides, linear open-chained on one side of a double stranded part with a single stranded hairpin on the respective other side of the double strand or a dumbbell-shaped partially single-stranded covalently closed chain of deoxyribonucleic acids.

The non-coding sequence of deoxyribonucleic acids may comprise at least three of said sequence motifs $N^1N^2CGN^3N^4$.

The non-coding sequence of deoxyribonucleic may further be a linear open-chained non-coding sequence of deoxyribonucleic acids comprising at least one nucleotide in L-conformation.

At least one of the five terminal nucleotides located at the 5'- and/or the 3'-end of a DNA single strand of the linear open-chained non-coding sequence of deoxyribonucleic acids is in L-conformation. It is obvious for a person having ordinary skill in the art that this restriction to the terminal ends means that only within the terminal five nucleotides either on the 5'- and/or the 3'-end nucleotides in 1-confirmation are contained.

It is intended that the non-coding sequence of deoxyribonucleic acids may comprise at least one of the sequence of a.
(SEQ ID NO: 1)
GTTCCTGGAG ACGTTCTTAG GAACGTTCTC CTTGACGTTG GAGAGAAC
or b.
(SEQ ID NO: 2)
ACCTTCCTTG TACTAACGTT GCCTCAAGGA AGGTTGATCT TCATAACGTT GCCTAGATCA,
or c.
(SEQ ID NO: 3)
AACGTTCTTCGGGG CGTT,
or d.
(SEQ ID NO: 4)
AGGTGGTAAC CCCTAGGGGT TACCACCTTC ATCGTCGTTT

TGTCGTTTTG TCGTTCTT.

The non-coding sequence of deoxyribonucleic acids of the instant disclosure may have a length of 40 to 200 nucleotides or more specifically 48 to 116 nucleoides.

The above shown sequence of AACGTTCTTCGGGG CGTT may be part of the sequence (SEQ ID NO: 5)
CCTAGGGGTT ACCACCTTCA TTGGAAAACG TTCTTCGGGG

CGTTCTTAGG TGGTAACC CCTAGGGGTT ACCACCTTCA

TTGGAAAACG TTCTTCGGGG CGTTCTTAGG TGGTAACC.

It is intended that the sequence motif $N^1N^2CGN^3N^4$ may be part of a single stranded region of the non-coding sequence of deoxyribonucleic acids.

Another object of the instant disclosure is a method comprising the step of providing a non-coding sequence of deoxyribonucleic acids of the present disclosure simultaneously, alternating or successively with combination antiretroviral therapy and/or histone de-acetylase inhibitors.

The non-coding sequence of deoxyribonucleic acids may be provided prior to combination antiretroviral therapy and/or histone de-acetylase inhibitors. Alternatively, it is intended that the non-coding sequence of deoxyribonucleic acids may be provided alternatingly with combination antiretroviral therapy and/or histone deacetylase inhibitors.

A further object of the instant disclosure is a non-coding sequence of deoxyribonucleic acids with the above disclosed features for use as a medicament.

The use of a non-coding sequence of deoxyribonucleic acids of the instant disclosure for the manufacture of a pharmaceutical composition comprising the non-coding sequence of deoxyribonucleic acids and possibly additionally ARV and/or histone de-acetylase inhibitors is another object of the instant disclosure.

The pharmaceutical composition may be a vaccine and it is intended to use the non-coding sequence of deoxyribonucleic acids with the features as disclosed above as an adjuvant in therapeutic or prophylactic vaccination for the treatment of HIV-1.

BRIEF DESCRIPTION OF THE FIGURES

The disclosure will be further illustrated by examples and figures without being limited to the disclosed embodiments. A non-coding sequence of deoxyribonucleic acids of the present invention is labelled "MGN1703" in FIGS. 1-3, and as "dSLIM" in FIG. 4. It shows.

DESCRIPTION OF THE INVENTION

The instant invention provides a compound and method for the treatment of viral infections. In particular, the invention relates to retroviral infection and the treatment of viral latency. The provided non-coding sequences of deoxyribonucleotides shall substantially augment NK cell activity and HIV-specific CD8+ cell cytotoxic activity leading to enhanced killing of HIV-expressing cells.

Within the meaning of the present disclosure a linear open-chained DNA sequence is designated as oligonucleotide, abbreviated with ODN. Said DNA sequence can be single-stranded or partially or completely double-stranded. The terms oligo, oligonucleotide and oligodeoxynucleotide are used synonymously and do not indicate a limitation of the length of the corresponding DNA sequence. The single components of oligonucleotides are nucleotides.

An oligo can be manufactured synthetically or be partially or completely of biological origin, wherein a biological origin includes genetically based methods of manufacture of DNA sequences.

L-DNA or nucleotides in L-conformation refer to nucleotides, which comprises L-deoxyribose as the sugar residue instead of the naturally occurring D-deoxyribose. L-deoxyribose is the enantiomer (mirror-image) of D-deoxyribose. Oligonucleotides partially or completely consisting of nucleotides in L-conformation can be partially or completely single- or double-stranded; however, nucleotides in L-conformation cannot hybridize to nucleotides in D-conformation (Hauser et al., Nucleic Acid Res. 2006 34: 5101-11). L-DNA is equally soluble and selective as D-DNA. Yet, L-DNA is resistant towards enzymatic exoactivity of naturally occurring enzymes, especially exonucleases, so L-DNA is protected against intracellular degradation (Urata et al., Nucleic Acids Res. 1992 20: 3325-32). Therefore, L-DNA is very widely applicable.

A "stem" according to the present disclosure shall be understood as a DNA double strand formed by base pairing either within the same oligonucleotide (which is then partially self-complementary) or within different oligonucleotides (which are partially or completely complementary). Intramolecular base-pairing designates base-pairing within the same oligonucleotide and base-pairing between different oligonucleotides is termed as intermolecular base-pairing.

A "loop" within the meaning of the present disclosure shall be understood as an unpaired, single-stranded region either within or at the end of a stem structure. A "hairpin" is a distinct combination of a stem and a loop, which occurs when two self-complementary regions of the same oligonucleotide hybridize to form a stem with an unpaired loop at one end.

A "solid phase" to which the nucleotides are covalently or non-covalently attached refers to, but is not restricted to, a column, a matrix, beads, glass including modified or functionalized glass, silica or silica-based materials including silicon and modified silicon, plastics (comprising polypropylene, polyethylene, polystyrene and copolymers of styrene and other materials, acrylics, polybutylene, polyurethanes etc.), nylon or nitrocellulose, resins, polysaccharides, carbon as well as inorganic glasses and plastics. Thus, microtiter plates are also within the scope of a solid phase according to the present disclosure.

Immunomodulation according to the present disclosure refers to immunostimulation and immunosuppression. Immunostimulation means preferentially that effector cells of the immune system are stimulated in order to proliferate, migrate, differentiate or become active in any other form. B cell proliferation for instance can be induced without co-stimulatory signals by immunostimulatory oligonucleotides, which normally require a co-stimulatory signal from helper thymocytes.

Immunosuppression on the other hand shall be understood as reducing the activation or efficacy of the immune system. Immunosuppression is generally deliberately induced to prevent for instance the rejection of a transplanted organ, to treat graft-versus-host disease after a bone marrow transplant, or for the treatment of autoimmune diseases such as, for example, rheumatoid arthritis or Crohn's disease.

An agonist within the meaning of the instant disclosure and in accordance with its common definition represents a chemical or molecule that binds to another molecule, like a receptor or ligand and thus activates the molecule. In contrast to an agonist that activates, an antagonist shall be understood as a chemical or molecule that blocks the interaction of the molecule to which the antagonist binds with a respective agonist. Depending on the context, an antagonist in the understanding of the instant invention may also result in the activation of a process, because the antagonist blocks the interaction of another antagonist with a receptor for instance.

The term "pharmaceutically applicable or acceptable salts" as used herein includes salts of a compound of the combination, which are prepared with relatively nontoxic (i.e. pharmaceutically acceptable) acids or bases, depending on the particular substituents found on the compounds of the present invention. If, for example, compounds of the present invention contain acidic functionalities, base addition salts may be obtained by contacting the neutral form of such compounds with a sufficient amount of the desired base, either neat or in a suitable inert solvent. Non-limiting examples of pharmaceutically acceptable base addition salts include sodium, potassium, calcium, ammonium, organic amino, or magnesium salt, or a similar salt. If compounds of the present invention contain basic functionalities, acid addition salts may be obtained by contacting the neutral form of such compounds with a sufficient amount of the desired acid, either neat or in a suitable inert solvent. Non-limiting examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic. malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoris acids and the like. Certain specific compounds of the present invention may contain both basic and acidic functionalities that allow the compounds to be converted into either base or acid addition salts. Contacting the salt with a base may regenerate the neutral forms of the compounds of the present invention or acid and isolating the parent compound in the conventional manner. The parent form of the compound differs from the various salt forms in certain physical properties, such as solubility in polar solvents, but otherwise the salts are equivalent to the parent form of the compound for the purposes of the present invention. The compounds of the present invention may possess chiral or asymmetric carbon atoms (optical centers) and/or double bonds. The racemates, diastereomers, geometric isomers and individual optical isomers are encompassed by the present invention. The compounds of the present invention may exist in unsolvated forms as well as solvated forms, including hydrated forms. In general, the solvated forms are equivalent to unsolvated forms and are also encompassed by the present invention. The compounds of the present invention may furthermore exist in multiple crystalline or amorphous forms.

Deoxyribonucleic acid molecules, consisting of a partially single-stranded, dumbbell-shaped, covalently closed chain of deoxyribonucleoside residues, which contain one or more sequences of the base sequence $N^1N^2CGN^3N^4$, wherein $N^1N^2$ is an element from the GT, GG, GA, AT or AA group, $N^3N^4$ is an element from the CT or TT group, as well as C deoxycytosine, G deoxyguanosine, A deoxyadenosine and T deoxythymidine, shall be used in combination with antiretroviral drugs and/or histone de-acetylase inhibitors.

The deoxyribonucleic acid molecules relating to the instant disclosure may have a length of up to 200 nucleotides. In particular, sequences with a length between 48 and 116 nucleotide are intended.

The dumbbell-shaped non-coding sequences of deoxyribonucleic acid molecules may comprise the base sequence $N^1N^2CGN^3N^4$ is their single-stranded regions.

The immunostimulation may take place in vitro, ex vivo or in vivo.

The instant disclosure provides also linear open-chained DNA sequence comprising at least one CpG motif and at least one nucleotide in L-conformation. Due to the partial/complete L-conformation, the DNA sequence is partially or fully resistant to exonucleases. In case that the construct has on one end of a double strand a single stranded-loop, the end is also protected against degradation. Thereby, the ODNs are in total protected against cellular degradation without having the need to use a phosphorothioate backbone, which has been shown to be toxic. In addition, the ODNs only consist of a minimum number of nucleotides, which makes them small and thereby easy to transfect into cells.

The non-coding sequence of deoxyribonucleic acids comprising at least one sequence motif $N^1N^2CGN^3N^4$ can be single-stranded or partially or completely double-stranded. This includes base-pairing within the same molecule (intra-molecular) or within different molecules (intermolecular) or any combination thereof. It is also possible that the construct comprises at least one unpaired, single-stranded region. As a further embodiment, hairpin structures are included. Due to the partial or complete L-conformation, a longer half-life of the construct is ensured as nucleotides in L-conformation are not subject to degradation.

It is also within the scope of the instant disclosure that at least two molecules, which are single-stranded or partially or completely double-stranded can ligate to each other to form multimeric constructs. These multimeric constructs thus incorporate at least as many CpG motifs as ligation partners, tightly packed within one molecule, and are therefore expected to elicit also a considerable immune response as part of the combination with T-cell regulators. The resulting single-stranded or partially or completely double-stranded multimeric constructs can either be covalently closed comprising nucleotides in L-conformation within the molecule or open multimeric constructs comprising nucleotides in L-conformation at the 5'- and/or the 3'-end for protection against cellular degradation.

The disclosure further comprises chemical modifications of at least one nucleotide in the non-coding sequence of deoxyribonucleic acids comprising at least one sequence motif $N^1N^2CGN^3N^4$ with a functional group selected from the group comprising carboxyl, amine, amide, aldimine, ketal, acetal, ester, ether, disulfide, thiol and aldehyde groups. This allows coupling of the DNA construct to a compound selected from the group comprising peptides, proteins, carbohydrates, antibodies, synthetic molecules, polymers, micro projectiles, metal particles or a solid phase by, for example, adsorption, covalent or ionic bonding.

The modification can be specifically selected for the respective purpose. The construct can thus be used, for example, to shuttle other molecules to the specifis cell responding to the CpG motif/s incorporated. In addition, it is possible by such modifications to couple the construct to micro projectiles, which can be used to transfer the construct into the cell. The construct can also be coupled to a solid phase, e.g. a microtiter plate.

Figure 1A:
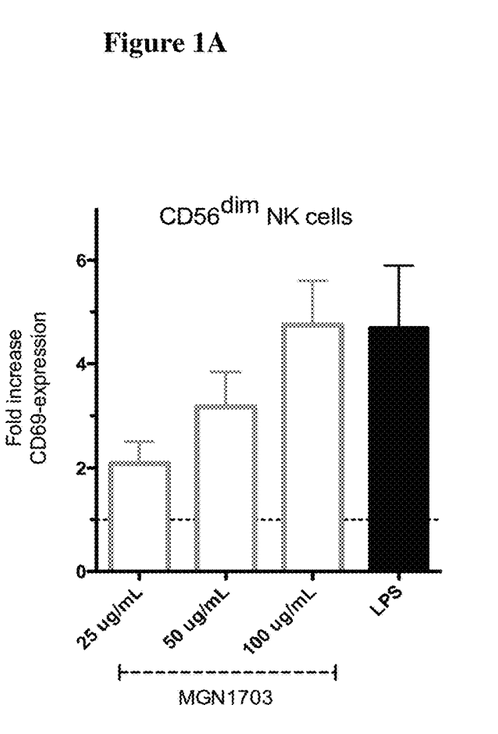
FIG. 1A/B MGN1703 upregulates CD69 expression, a marker of cell activation, on peripheral blood immune effector cells (natural killer cells and CD8 T cells)
Figure 1B:
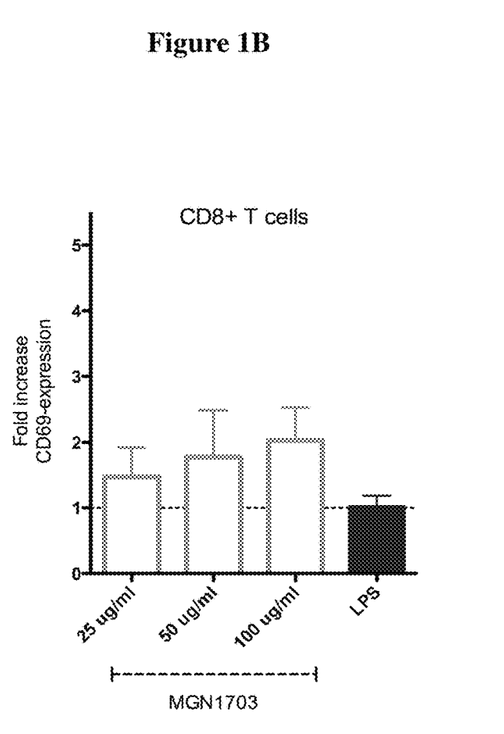

FIG. 1 shows that MGN1703 upregulates CD69 expression, a marker of cell activation, on peripheral blood immune effector cells. Total PBMC (n=5 separate donors) were stimulated with MGN1703 or LPS. Following stimulation, cells were analyzed via flow cytometry and CD69 expression on NK cells (left) and CD8+ T cells (right) were characterized. Depicted is mean fold above media control.

Figure 2:
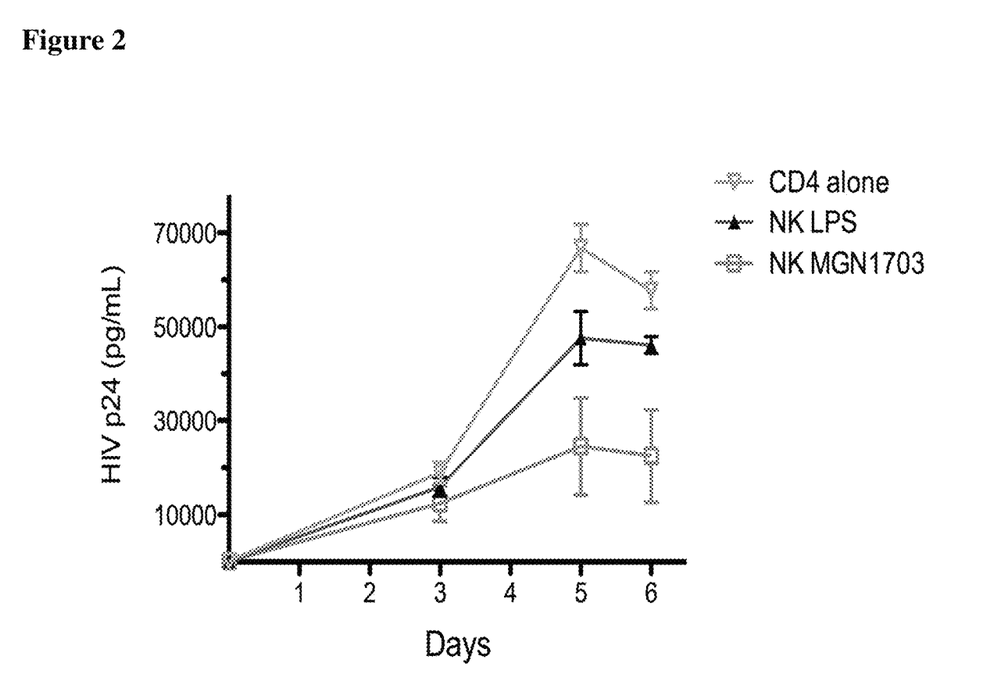
FIG. 2 MGN1703 stimulated NK cells inhibit the spread of HIV

FIG. 2 shows that MGN1703 stimulated NK cells inhibit the spread of HIV. CD4-depleted PBMC (one representative donor with SD shown) were stimulated with MGN1703 or LPS. Following stimulation, the cells were incubated with autologous HIV-infected CD4+ cells. HIV capsid protein (Gagp24) was quantitated in culture supernatants over time as a measure of virus spread.

Figure 3:
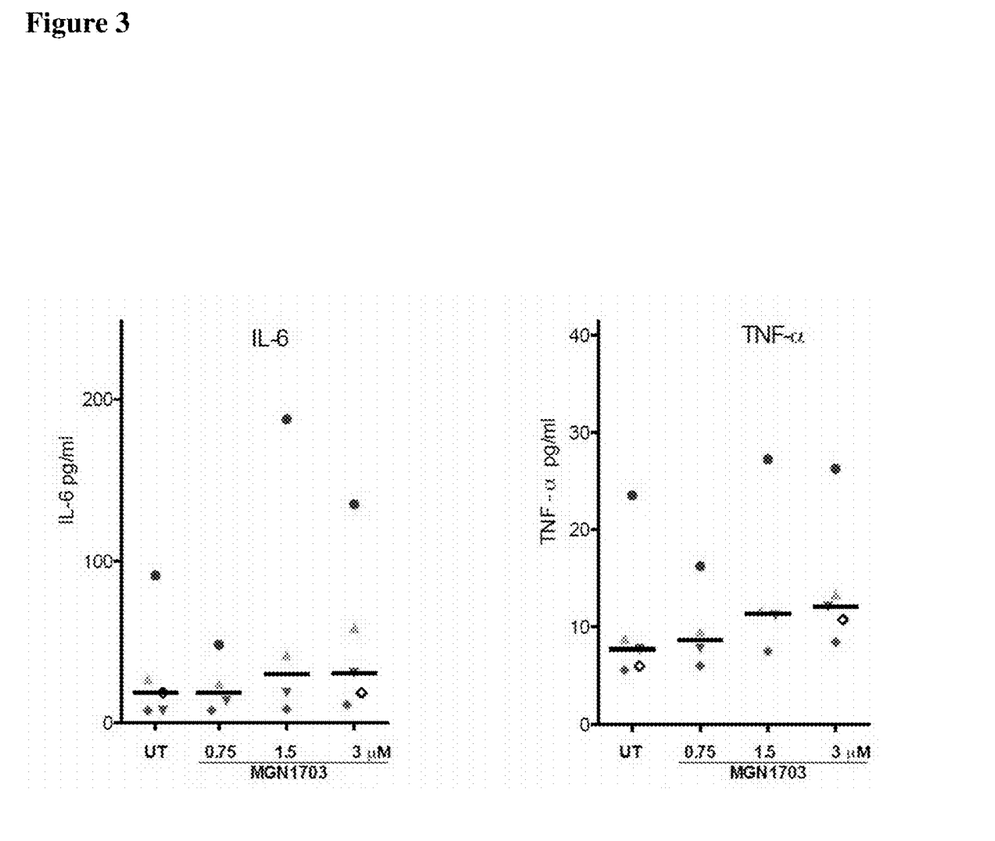
FIG. 3 Non-coding DNA constructs of the present invention cause negligible changes in pro-inflammatory cytokines IL-6 and TNF α.

FIG. 3 shows that the non-coding DNA constructs have almost no effect on the pro-inflammatory cytokines IL-6 (FIG. 3A) and TNFα (FIG. 3B). "UT" denotes untreated controls, "MGN1703" denotes the non-coding DNA constructs applied in concentrations of 0.75 µM, 1.5 µM, and 3 µM from left to right. Thus, the use of a non-coding immunostimulating sequence of deoxyribonucleotides activated viral infected cells without initiating an unintended cytokine based inflammation.

Figure 4A:
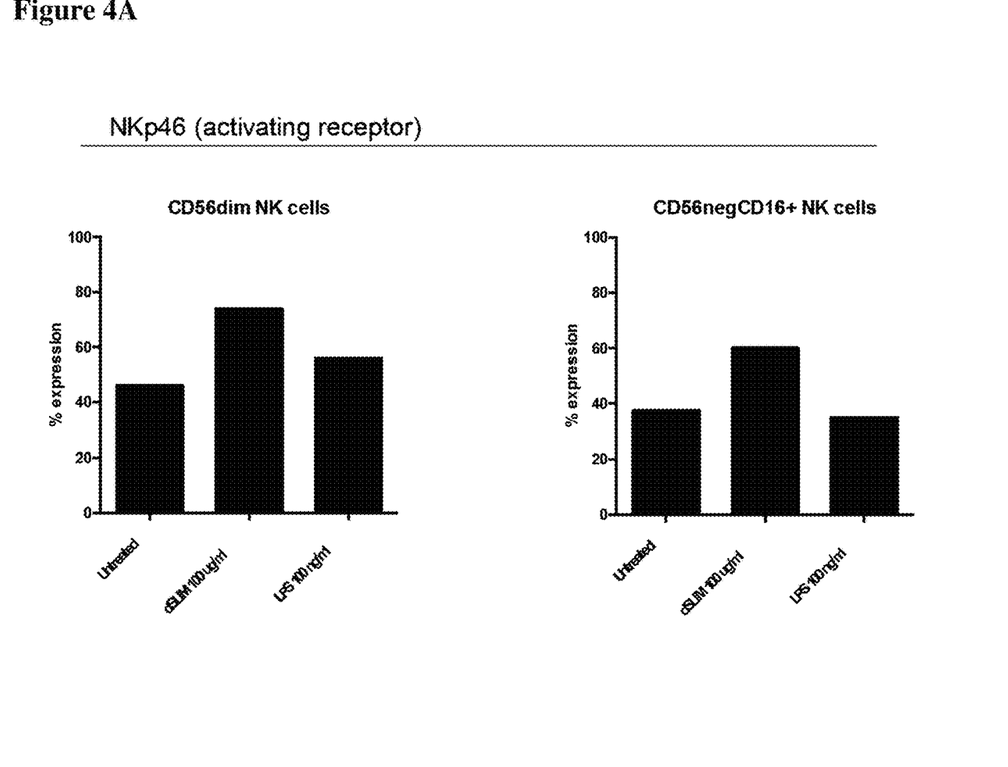
FIG. 4A/B Activating effect of stimulation of NK cells with non-coding immunostimulating sequence of DNA FIG. 5A/B/C Treatment of NK cells with non-coding DNA constructs. The non-coding DNA constructs enhance NK cell-mediated killing of HIV-1 producing autologous CD4+ T cells.
Figure 4B:
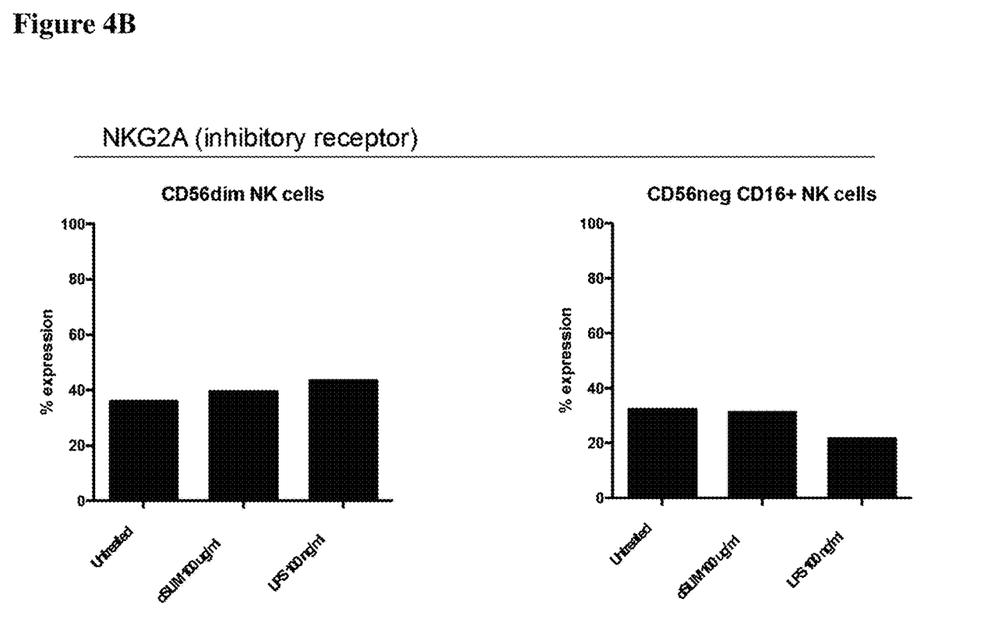

In order to confirm the activating effect of stimulating NK cells with noncoding immunostimulating sequence of deoxyribonucleotides, the effect on activating or inhibitory receptors of NK cells was investigated. FIGS. 4A and 4B show that only the expression of activating receptors is increased by the non-coding DNA sequences.

Figure 5A:
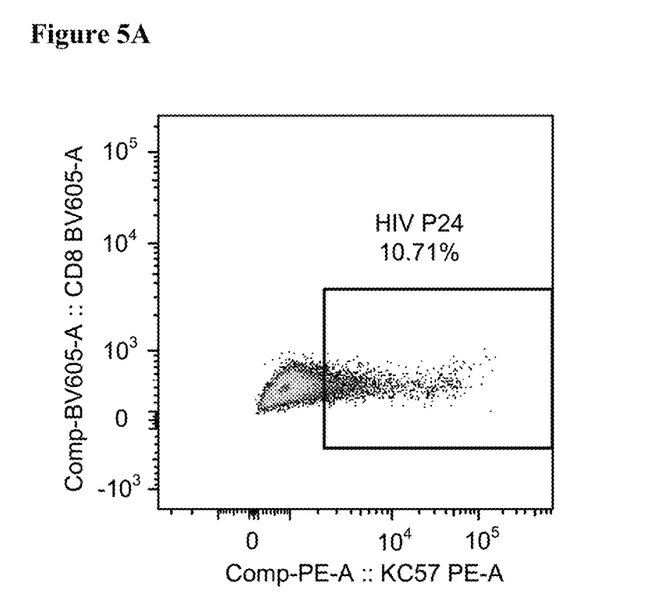
Figure 5B:
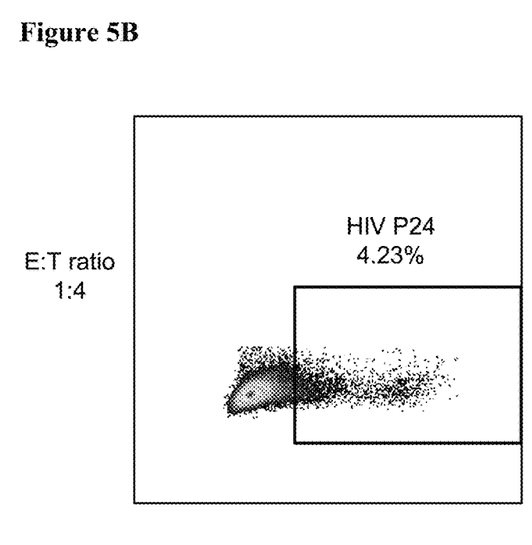
Figure 5C:
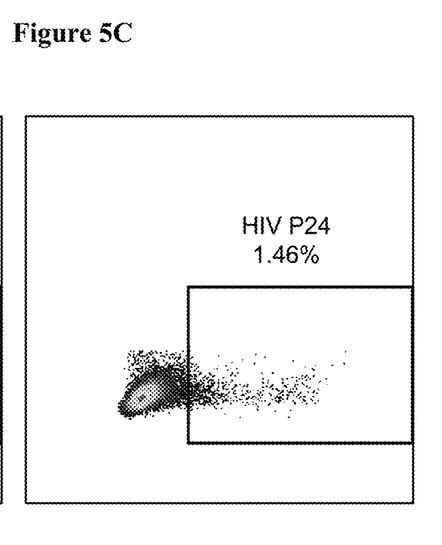

FIG. 5 shows the results of experiments that were conducted to confirm that the viral inhibition shown in FIG. 2 was a result of HIV-specific killing and not unspecific CD4 T cell death. HIV infected cells were collected on day 6 and stained for intracellular P24 antigen. FIG. 5A shows CD4 T-cells which were cultured alone, FIG. 5B shows CD4 T-cells cultured together with untreated NK cells and FIG. 5C shows CD4 T-cells cultured together with dSLIM treated NK cells. The square in each figure gates the population of HIV infected cells. Their percentage on the total population is indicated above the square.

The results in FIG. 5 confirm that the treatment of NK cells with non-coding DNA constructs according ton the present disclosure is suitable to reduce considerably the number of HIV infected cells.

In essence, the instant disclosure demonstrates that the treatment of viral infections leading to latency can be supported by the treatment with non-coding DNA constructs according to the present disclosure. Infected cells will be activated or "demasked" so that the immune system will be able to kill them. Thus the combinatorial treatment of HIV infections with cART for instance is supported by applying immunostimulating non-coding DNA.

Referring to the results described as prior art where cART and HDACi were combined, it seems to be possible that the combinatorial treatment of those two components of HIV treatment with immunostimulating non-coding DNA constructs will be beneficial for the HIV treatment. Corresponding experiments aiming at proving such a beneficial effect are currently performed.

It has to be noted that the non-coding immunostimulating DNA constructs of the instant disclosure have the advantage of avoiding pro-inflammatory cytokine stimulation. In contrast, non-coding DNA constructs that are stabilized against nuclease degradation by chemical modifications are known to cause pro-inflammatory cytokine release.

It was surprising that the stimulation of latent retroviral infected cells did not result in an accelerated progression of the HIV infection to AIDS. It was not predictable that the stimulation with constructs according to the above disclosure enhances the success rates of HIC treatment with cART and/or HDACi.

The invention claimed is:

1. A method of treating a latent human immunodeficiency virus 1 (HIV-1) infection in a patient in need thereof, comprising administering to the patient a non-coding sequence of deoxyribonucleic acids comprising

```
                                              (SEQ ID NO: 5)
CCTAGGGGTT ACCACCTTCA TTGGAAAACG TTCTTCGGGG

CGTTCTTAGG TGGTAACC CCTAGGGGTT ACCACCTTCA

TTGGAAAACG TTCTTCGGGG CGTTCTTAGG TGGTAACC
``` in combination with combination antiretroviral therapy.

2. The method of claim 1, wherein the non-coding sequence of deoxyribonucleic acids has a length of up to 200 nucleotides.

3. The method of claim 1, wherein the non-coding sequence of deoxyribonucleic acids has a length of 116 nucleotides.

4. The method of claim 1, where the non-coding sequence of deoxyribonucleic acids is part of a single stranded region.

5. The method of claim 1 comprising administering the non-coding sequence of deoxyribonucleic acids simultaneously, alternating or successively with combination antiretroviral therapy.

6. The method of claim 5, wherein the non-coding sequence of deoxyribonucleic acids is administered prior to combination antiretroviral therapy.

7. The method of claim 1, wherein the non-coding sequence of deoxyribonucleic acids is administered as an adjuvant in therapeutic or prophylactic vaccination.

* * * * *